United States Patent
Schug et al.

(10) Patent No.: US 12,115,329 B2
(45) Date of Patent: *Oct. 15, 2024

(54) SYSTEM FOR CLEANSING WOUNDS

(71) Applicant: MEDAXIS AG, Baar (CH)

(72) Inventors: Martin Schug, Meggen (CH); Beat Widmer, Lucerne (CH); Claudio Steiner, Baar (CH); Roman Good, Zurich (CH)

(73) Assignee: MEDAXIS AG, Baar (CH)

( * ) Notice: Subject to any disclaimer, the term of this patent is extended or adjusted under 35 U.S.C. 154(b) by 1042 days.

This patent is subject to a terminal disclaimer.

(21) Appl. No.: 17/016,159

(22) Filed: Sep. 9, 2020

(65) Prior Publication Data
US 2020/0405945 A1  Dec. 31, 2020

Related U.S. Application Data

(63) Continuation-in-part of application No. 14/912,772, filed as application No. PCT/EP2014/068853 on Sep. 4, 2014, now Pat. No. 10,987,463.

(30) Foreign Application Priority Data

Sep. 6, 2013 (EP) .................................. 13183379

(51) Int. Cl.
*A61M 3/02* (2006.01)
*A61M 1/00* (2006.01)

(52) U.S. Cl.
CPC ............ *A61M 3/0279* (2013.01); *A61M 1/85* (2021.05); *A61M 3/0254* (2013.01);
(Continued)

(58) Field of Classification Search
CPC ...... A61M 1/77; A61M 1/774; A61M 3/0283; A61M 27/00; A61F 2013/00536; A61B 90/05
See application file for complete search history.

(56) References Cited

U.S. PATENT DOCUMENTS

| | | |
|---|---|---|
| 3,818,911 A | 6/1974 | Fournier |
| 3,891,331 A | 6/1975 | Avery |
| (Continued) | | |

FOREIGN PATENT DOCUMENTS

| | | |
|---|---|---|
| CN | 202113477 U | 1/2012 |
| EP | 2251142 A1 | 11/2010 |
| (Continued) | | |

OTHER PUBLICATIONS

International Search Report for International Application No. PCT/EP2014/068853, mailed Nov. 18, 2014.

(Continued)

*Primary Examiner* — Laura A Bouchelle
(74) *Attorney, Agent, or Firm* — MARSHALL, GERSTEIN & BORUN LLP

(57) ABSTRACT

A system for cleansing wounds with a fluid jet includes a pressure pump (900) for generating a fluid jet, a handpiece body (200) with a nozzle (204) for emerging the fluid jet, a fluid line (90) connecting the pressure pump (900) with the handpiece body (200), an adapter (700) holding a porous body (510), the adapter (700) being releasably connected to the handpiece body (200). The adapter (700) and the porous body (510) comprise a free inner space (770, 570) into which the fluid jet emerges when leaving the nozzle (204). The adapter (700) is at least partially transparent, thereby enabling a view into the inner space of the adapter and the porous body. The system according to the invention combines the advantages of cleansing by a fluid jet with the advantages of mechanical cleansing and, at the same time, provides effective protection against aerosols.

17 Claims, 18 Drawing Sheets

(52) U.S. Cl.
CPC ............. *A61M 3/0283* (2013.01); *A61M 1/77* (2021.05); *A61M 1/774* (2021.05)

(56) References Cited

U.S. PATENT DOCUMENTS

| | | | |
|---|---|---|---|
| 5,037,431 A | 8/1991 | Summers et al. | |
| 5,380,300 A | 1/1995 | Pritchard et al. | |
| 5,489,280 A * | 2/1996 | Russell | A61M 35/003 |
| | | | 604/289 |
| 5,941,859 A * | 8/1999 | Lerman | A61M 3/0287 |
| | | | 604/289 |
| 6,099,494 A | 8/2000 | Henniges et al. | |
| 6,210,381 B1 * | 4/2001 | Morse | A61B 90/80 |
| | | | 604/289 |
| 6,293,929 B1 * | 9/2001 | Smith | A61M 3/0287 |
| | | | 604/289 |
| 6,371,675 B1 | 4/2002 | Hoang et al. | |
| 7,261,701 B2 | 8/2007 | Davis et al. | |
| 10,987,463 B2 * | 4/2021 | Schug | A61B 17/3203 |
| 2003/0049069 A1 | 3/2003 | Osei et al. | |
| 2005/0276836 A1 | 12/2005 | Wilson et al. | |
| 2006/0264851 A1 | 11/2006 | Coleman | |
| 2007/0100300 A1 | 5/2007 | Hashemian | |
| 2008/0212411 A1 | 9/2008 | Polonio et al. | |
| 2009/0324319 A1 | 12/2009 | Houde et al. | |
| 2011/0066121 A1 | 3/2011 | Hoang et al. | |
| 2014/0234004 A1 | 8/2014 | Thorpe et al. | |
| 2016/0199566 A1 * | 7/2016 | Schug | A61B 17/3203 |
| | | | 604/289 |
| 2016/0346794 A1 | 12/2016 | Moser et al. | |
| 2017/0080144 A1 | 3/2017 | Moser et al. | |
| 2017/0354432 A1 | 12/2017 | Moser et al. | |
| 2017/0356443 A1 | 12/2017 | Moser et al. | |
| 2018/0126392 A1 | 5/2018 | Moser et al. | |

FOREIGN PATENT DOCUMENTS

| | | |
|---|---|---|
| JP | 2000-24073 A | 1/2000 |
| JP | 2002-514094 A | 5/2002 |
| WO | WO-82/03316 A1 | 10/1982 |
| WO | WO-97/48426 A2 | 12/1997 |
| WO | WO-2004/037095 A2 | 5/2004 |
| WO | WO-2008/074484 A1 | 6/2008 |
| WO | WO-2013/084945 A1 | 6/2013 |

OTHER PUBLICATIONS

English Translation of the International Preliminary Report on Patentability for International Application No. PCT/EP2014/068853, date of issuance Mar. 8, 2016.

Advantages of Polyethylene Pipe, 2020, Charter Plastics, URLhttp://www.charterplastics.conn/advantages-of-polyethylene-pipe/ (Year: 2020).

* cited by examiner

SYSTEM FOR CLEANSING WOUNDS

CROSS REFERENCE TO RELATED APPLICATION

This application is a continuation-in-part of U.S. patent Ser. No. 14/912,772, the US national phase of International Application No. PCT/EP2014/068853, filed Sep. 4, 2014, which claims priority to European Patent Application EP 13183379.0, filed Sep. 6, 2013, the entirety of each of which is hereby incorporated by reference in its entirety.

TECHNICAL FIELD

The present invention relates to a system for cleansing wounds with a fluid jet and a unit of such a system.

PRIOR ART

Wound cleansing/debridement and wound rinsing/wound toilet refers to medical procedures for removing infected, damaged or dead (necrotic) tissue from ulcers, burns and other wounds or in cases of organ decay. There are numerous general approaches for cleansing wounds, e.g. mechanical sharp approaches using a scalpel or a sharp spoon, enzymatic or chemical, or autolytic, biosurgical, mechanical approaches using pads and a fluid jet.

EP 2 251 142 shows a handpiece for cleansing wounds with a high-pressure micro-fluid jet, wherein an emergence opening is arranged at the front end of the handpiece, through which a fluid jet can emerge.

Depending on the consistency, location, age and nature of the wound coating, the fluid jet has to be applied for different lengths of time and at different strengths in order to ensure sufficiently effective and sufficiently gentle detachment and removal of the wound coating while at the same time providing maximum protection of the tissue.

However, the fluid jet on its own is often not sufficient to achieve the desired cleansing effect. In this case, additional mechanical cleansing elements, e.g. pads, scalpels or sharp spoons, are used. This is awkward, however, since the operator needs a second hand for this purpose. This hand can be his own or that of an assistant. This complicates the wound cleansing. Moreover, this treatment in most cases causes the patient pain, and there is the danger of the tissue being unnecessarily damaged.

In case of cleansing wounds with a fluid jet, coatings or particles are removed from the wound, with aerosols being created in the process. It is important to ensure that the environment is contaminated as little as possible by these aerosols, since these constitute a danger to the patient or the operating staff. The prior art discloses numerous methods for reducing or preventing contamination of the environment by the aerosols. Such methods are e.g. returning the liquid, a shielding treatment tent with an exhaust lock, or the arrangement of the fluid jet and of the suction system in a covering hood. Said methods are complicated, since liquid not only has to be supplied, it also has to be returned.

Examples of wound cleansing devices involving a return of the liquid are disclosed in WO 2008/074284 and in WO 2004/037095.

SUMMARY OF THE INVENTION

It is therefore desired to improve the cleansing of a wound and to prevent a spread of the aerosols.

An inventive system for cleansing wounds with a fluid jet, the system comprises
 a pressure pump for generating a fluid jet,
 a handpiece body with a nozzle for emerging the fluid jet,
 a fluid line connecting the pressure pump with the handpiece body and
 an adapter holding a porous body, the adapter being releasably connected to the handpiece body.
The porous body comprises a lower surface, which is shaped to be placed on a patient's skin around a wound to be cleaned,
 wherein the adapter and the porous body comprise a free inner space into which the fluid jet emerges when leaving the nozzle, and
 wherein the adapter is at least partially transparent, thereby enabling a view into the inner space of the adapter and the porous body.

The handpiece body, the adapter and the porous body form the handpiece.

The handpiece according to one embodiment comprises a main body, which has a front end with an emergence opening for the emergence of the fluid jet. A porous body is present on the front end of the handpiece. This porous body surrounds the emergence opening and it protrudes beyond the latter in the direction of the fluid jet outlet and forms a space through which the fluid jet can pass unimpeded.

The system and the handpiece according to the invention combines the advantages of cleansing and treatment with a fluid jet, in particular a microfluidic jet, with the advantages of mechanical wound cleansing in a simple and cost-effective handpiece.

The inventive system and unit can be used according to a method in which the wound is treated simultaneously by a fluid jet emerging from the handpiece and by a porous body arranged on the handpiece.

Preferably, the pressure of the fluid jet can be set at different levels depending on the particular use. Thus, certain wounds can be treated with high pressure, whereas others can be treated with low pressure.

By simultaneously treating the wound with a fluid, in particular an aqueous solution or a treatment solution, e.g. a sterile saline solution, and mechanically treating the wound with the porous body, the tissue, in particular the vital and granulating tissue, is still protected optimally, compared to all the mechanically sharp methods. The combined application of the fluid jet and the mechanically acting porous body not only increases the cleansing action but also additionally activates and stimulates the tissue. This promotes wound healing and accelerated wound closure, as a result of which the overall treatment costs are reduced.

The wound cleansing is improved and the treatment time shortened, while wound healing is additionally promoted. Protection is at the same time provided against aerosols, and it is therefore possible to dispense with the use of a cover or a protective tent, particularly when cleansing relatively small wounds.

The mechanical treatment can be targeted locally and can be applied only for as long as is strictly necessary. It is not necessary for the mechanical treatment to be applied throughout the treatment with the fluid.

Since the body is porous, aerosols that arise can be trapped in the body. The porous body can moreover take up fluids and tissue particles. An additional suction system can be omitted. Since the body surrounds the fluid jet and protrudes beyond the emergence opening, it offers optimal protection in the smallest possible space. The porous body can be configured with open pores on its outer circumference. However, its outer jacket can also be formed by a tight outer skin. For example, it can be covered by a layer of silicone or by a film. The outer skin can also be generated by a spray-on skin, by applying a varnish, by melting or by other known techniques.

It is possible to provide additionally a suction system. This additional suction system can increasingly carry away aerosols, fluids, biofilms or other substances present in the wound. If suction is provided, it takes place, in preferred embodiments, in the porous body. For this purpose, the porous body is preferably provided with the tight outer skin. The suction can take place through the pores that are present anyway in the porous body. In preferred embodiments, the porous body has suction channels with a larger diameter than the pores, wherein these suction channels preferably extend approximately parallel to the jet direction of the fluid jet. Preferably, the suction channels extend parallel to the jacket surface of the porous body. In further embodiments, radially extending suction channels are alternatively or additionally present which open into the space enclosed by the porous body, which space is also referred to as the first through-opening. By virtue of the suction, the porous body is saturated less quickly and the handpiece can be used for longer.

The fluid jet is preferably a microfluidic jet, in particular a high-pressure or low-pressure microfluidic jet. The pressure range is usually from 1 to 300 bar. The fluid jet is preferably a microfluidic jet, i.e. a fluid jet with a diameter of approximately 0.05 mm to 0.15 mm upon emergence from the emergence opening. The fluid jet is usually a single solid jet. However, it is also possible for a conical, hollow conical or flat jet to be used as a single or multiple jet.

In some embodiments, the emergence opening of the fluid jet is designed such that the jet extends approximately parallel to the longitudinal central axis of the porous body. In other preferred embodiments, it extends at an angle with respect to this longitudinal central axis. The angle is preferably approximately 45°. Compared with the emergence direction parallel to the central axis, this angled emergence direction results in a different treatment action and abrasion action on the wound surface. Thus, a fluid jet emerging at an angle of 45° with respect to the longitudinal central axis, and thus also striking the wound surface at this angle, has a peeling action.

The porous body can be designed in one piece. It can also be composed of several subsidiary bodies, which are arranged at the front end of the handpiece and together form a closed body surrounding the emergence opening. The porous body can also have interruptions. However, it is preferably mostly or completely closed, such that the emergence opening is surrounded seamlessly by the porous body.

The porous body is preferably made of a material like a sponge, fleece or knit. The material is preferably synthetic. These materials have favorable mechanical properties for wound cleansing. They are sufficiently firm to have the required inherent stability, but they are flexible enough not to cause any injuries upon contact with the wound. On account of the porosity, they are also distinguished by an increased surface area, which favors the cleansing action.

The porous body can be provided with a coating having a disinfecting action.

Preferably, the porous body can be arranged with an inner surface on the front end of the handpiece. Additionally or alternatively, it can be arranged on the handpiece via a rear face directed toward the front end of the handpiece. If only the inner surface is used for the arrangement, the porous body can, for example, be pushed over the front end of the handpiece. The use of the rear face of the porous body as a contact surface increases the overall surface area, which is advantageous, for example, in the case of a cohesively bonded connection.

The front end of the handpiece is preferably transparent, which permits a better view of the wound that is to be cleaned.

The porous body is preferably arranged in a fixed manner or releasably on the front end of the handpiece. A releasable connection between the front end of the handpiece and the porous body affords the advantage that the porous body is exchangeable and can be disposed of after use, or different porous bodies can be used for different applications. For example, different porous bodies can be used with the same handpiece, said porous bodies differing from one another in terms of porosity, shape, material and/or degree of abrasion.

However, the porous body can also be connected to the front end of the handpiece with a form fit or force fit. This simplifies production, since it is possible to dispense with complicated connections.

Preferably, an outer contour of the front end is larger than the inner contour of the porous body containing the inner surface. In this way, the porous body can be arranged with a clamping action on the front end of the handpiece. Preferably, however, the porous body is movable, which makes it possible to adjust the distance from the emergence opening to a contact surface of the porous body. Thus, for example, it can be pushed down toward the wound to permit the mechanical treatment of the wound and, when the fluid jet is used on its own, it can be withdrawn from the area of contact with the wound. It is thus possible to set a distance that is adapted specifically to the patient or to the wound.

Preferably, the front end of the handpiece has a recess for receiving the porous body. This makes it easier to fit the porous body on the front end of the handpiece. In the case of a fixed connection, a recess makes positioning easier and increases the contact surface area between the front end of the handpiece and the porous body. In the case of a releasable connection, a recess permits the formation of a form-fit connection.

Preferably, the porous body can be arranged on the front end of the handpiece by means of an adapter. The adapter has the advantage that it is easily detachable together with the porous body. Thus, a form-fit or force-fit connection can be realized between the front end of the handpiece and the adapter. The adapter is preferably configured such that it completely covers the front end of the handpiece except for an emergence opening. This affords the advantage that the front part is not contaminated by the aerosols that arise. However, the adapter can also be configured such that an area of the front end of the handpiece is accessible from the front.

The body preferably has a substantially hollow cylindrical, conical or polyhedral shape. Cylindrical and conical shapes are easier to produce and assemble and are therefore more cost-effective. By contrast, polyhedral shapes can be specifically configured, for example in order to form areas of different stiffness in the porous body.

The porous body preferably has a contact area for contact with a wound, which contact area extends substantially perpendicularly with respect to the direction of the fluid jet outlet.

The porous body preferably has a contact area, for contact with a wound, that extends substantially at an angle other than 90° with respect to the direction of the fluid jet outlet. When, during cleansing, the contact area is then placed onto the wound to be cleaned, the fluid jet strikes the surface to be cleaned and does so at an angle. The angle between the fluid jet and the perpendicular on the surface to be cleaned can be 0° to 90°. For example, porous bodies with an angle of 5°, 10°, 15°, 30°, 45°, 60° or 75° can be made available to the user.

The porous body preferably has, in the contact area, an outwardly directed, circumferential front collar. The collar increases the stiffness of the porous body in the contact area. It likewise increases the area of the wound to be cleaned that can be covered by the porous body.

In another preferred embodiment, the porous body has a circumferential rear collar, which is inwardly directed in a rear area, for engaging in a corresponding recess of the front end. In this way, a releasable connection which can be easily produced is realized between the two elements. The shape of the collar must be such that a substantially form-fit connection can be realized. The collar can, for example, have a circular, polyhedral or helical shape. However, it can also be composed of several collars arranged in series.

A porous body as described above is preferably to be used with a handpiece as described above. The handpiece and the porous body form a coordinated unit. The handpiece preferably has a nozzle, which forms the emergence opening. Preferably, the handpiece, and in particular the front end of the handpiece, is stiff.

The porous body has an adapter for connection to the handpiece. Preferably, the adapter is connected cohesively to the porous body and forms an exchangeable unit with the latter. Different units can thus be quickly and easily exchanged.

The porous body preferably has a first through-opening, which forms the space. In this way, the fluid jet is not deflected by the porous body.

Further embodiments are set forth in the dependent claims.

BRIEF DESCRIPTION OF THE DRAWINGS

Preferred embodiments of the invention are described below with reference to the drawings, which serve only for illustrative purposes and are not to be interpreted as limiting the invention. In the drawings.

DESCRIPTION OF PREFERRED EMBODIMENTS

Figure 1:
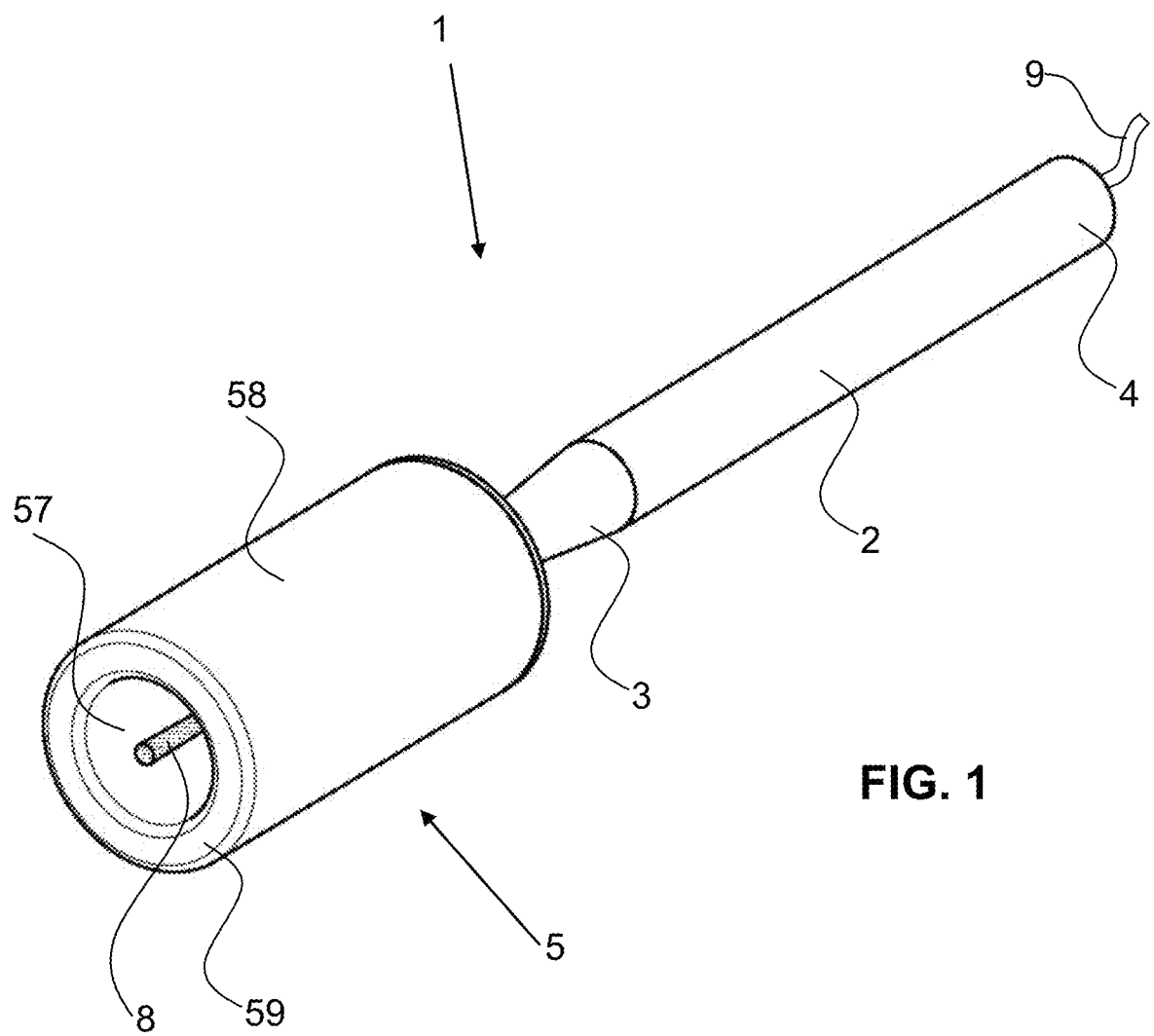
FIG. 1 shows a perspective view of a first embodiment of a handpiece according to the invention, with fluid jet.
Figure 2:
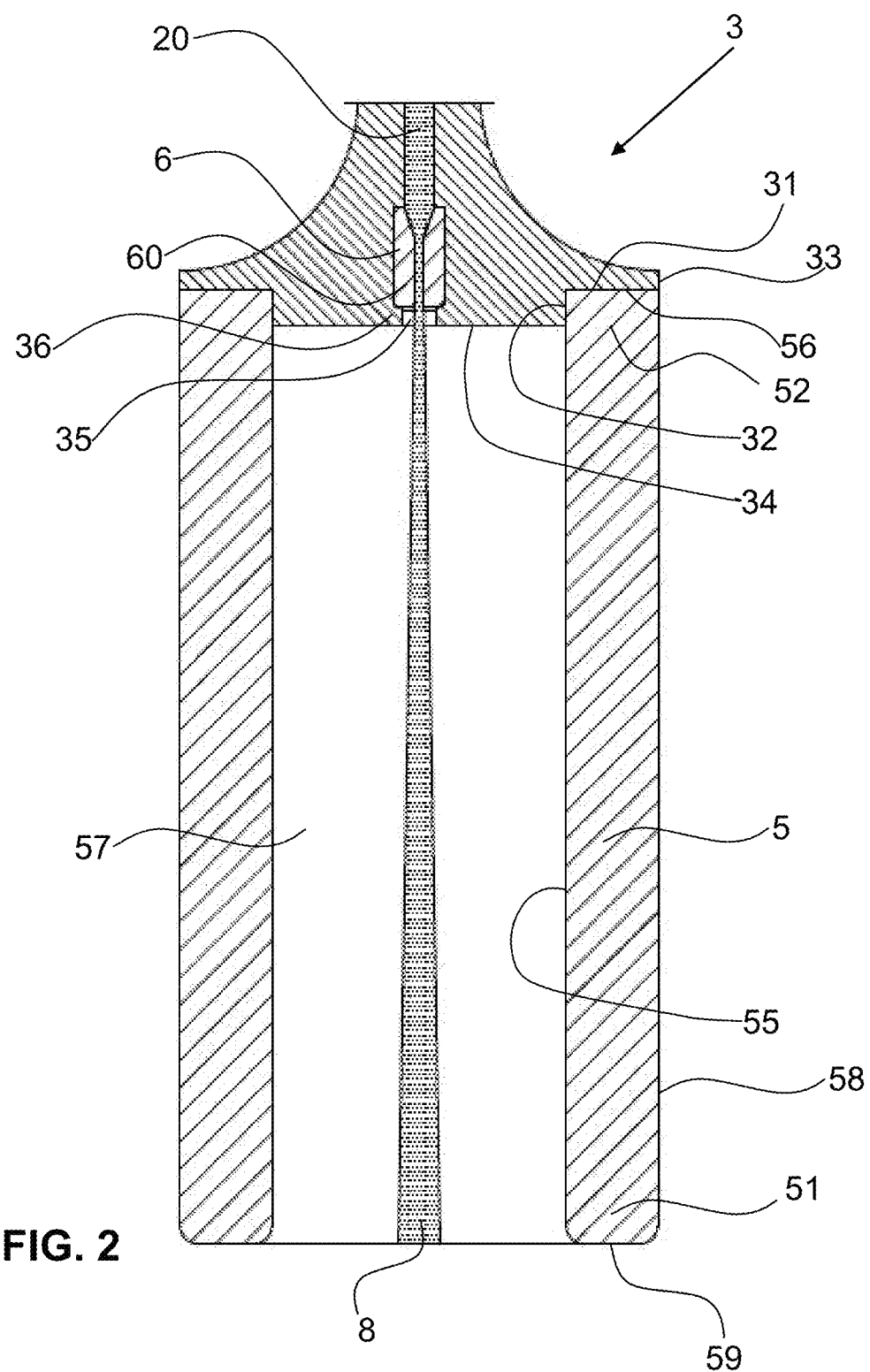
FIG. 2 shows a central sectional view of the front end of the handpiece with a porous body according to FIG. 1, with fluid jet.

FIG. 1 shows a perspective view of a first embodiment of a handpiece 1 according to the invention with fluid jet 8, while FIG. 2 shows a central sectional view of the front end 3 thereof. The handpiece 1 has a substantially cylindrical main body 2 for holding in one hand, with a front end 3 and a rear end 4. The front end 3 is preferably transparent. The front end 3 has an emergence opening 35 for the emergence of the fluid jet 8. The emergence opening 35 is arranged centrally in a first front face 34 of the handpiece 1. The handpiece 1 is designed in such a way that the fluid jet 8 flows out of the emergence opening 35 substantially collinearly with respect to the central axis of the main body 2.

A porous body 5 provided for gentle mechanical wound cleansing, and acting as a protective sleeve, is arranged at the front end 3. The porous body 5 has substantially the shape of a hollow cylinder with a first through-opening 57, which forms a space. With its rear area 52, it surrounds the emergence opening 35 and protrudes beyond the latter in the direction of the fluid outlet. The first front face 34 has a recess with a first axial limit surface 31 and a first radial limit surface 32 for receiving the porous body 5. The porous body 5 bears with an inner surface 55 on the first radial limit 32 of the front end 3 and bears with a rear face 56 on the first axial limit 31 of the front end 3. An outer surface 58 of the porous body 5 is designed flush with a first radial outer surface 33 of the front end 3.

In this illustrative embodiment, there is preferably a cohesively bonded connection between the front end 3 and the porous body 5. However, a force-fit and/or form-fit connection is also possible.

On a face lying opposite the rear area 52, the porous body 5 has a contact area 51. The latter has a contact surface 59 which is parallel to the first front face 34 of the front end 3 and which adjoins the inner surface 55 and the outer surface 58. The transitions between the contact surface 59 and the inner surface 55 and outer surface 58 are preferably rounded.

The front end 3 comprises a centrally arranged fluid channel 20 and, flush with the latter, a nozzle 6, which is in turn flush with the emergence opening 35. The substantially cylindrical nozzle 6 is received in a known manner in the front end 3 of the handpiece 1, and its position in the jet direction is defined by a front abutment 36. The nozzle 6 has a nozzle channel 60 arranged centrally therein. The design of this channel defines the emergence geometry of the fluid jet 8.

FIG. 1 further shows that the rear end 4 has a fluid line 9, wherein the fluid line 9 ensures the supply of fluid to the handpiece 1. The following embodiments of the handpiece 1 according to the invention likewise have a fluid line 9 at the rear end 4. However, it is not shown.

Figure 3:
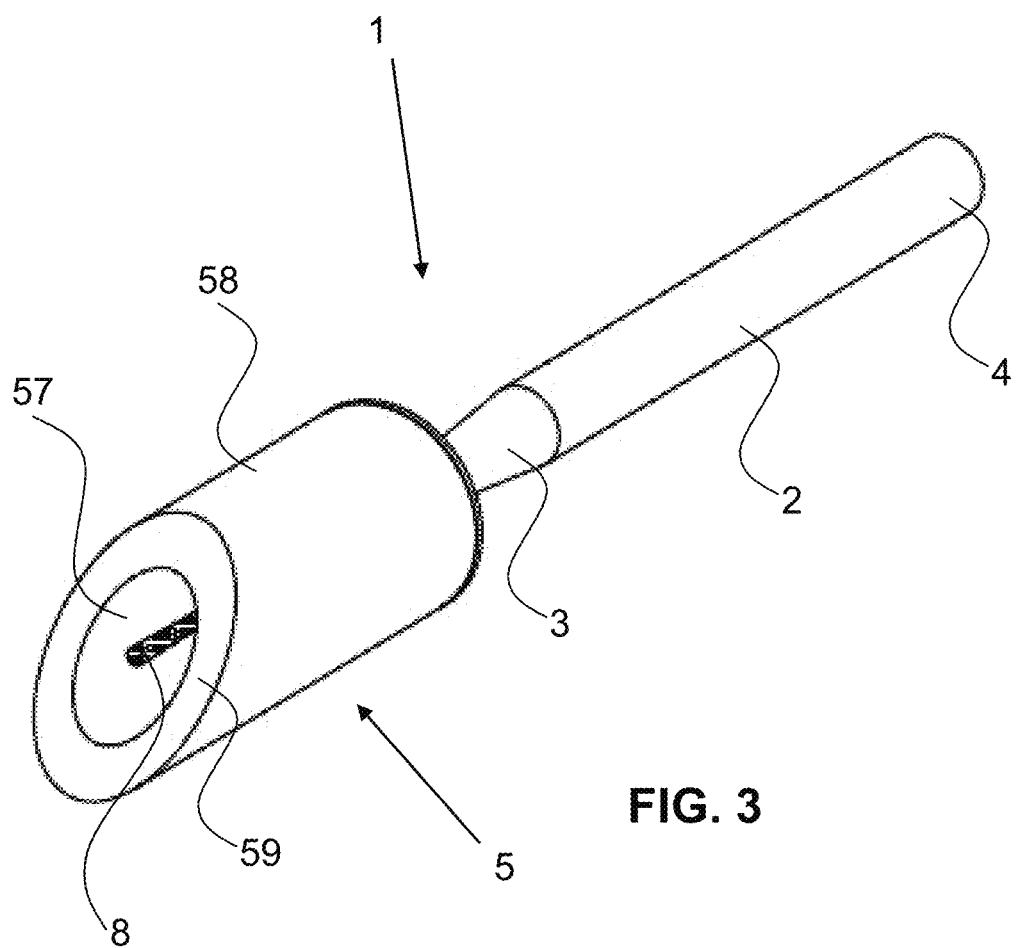
FIG. 3 shows a perspective view of a second embodiment of a handpiece according to the invention, with fluid jet.
Figure 4:
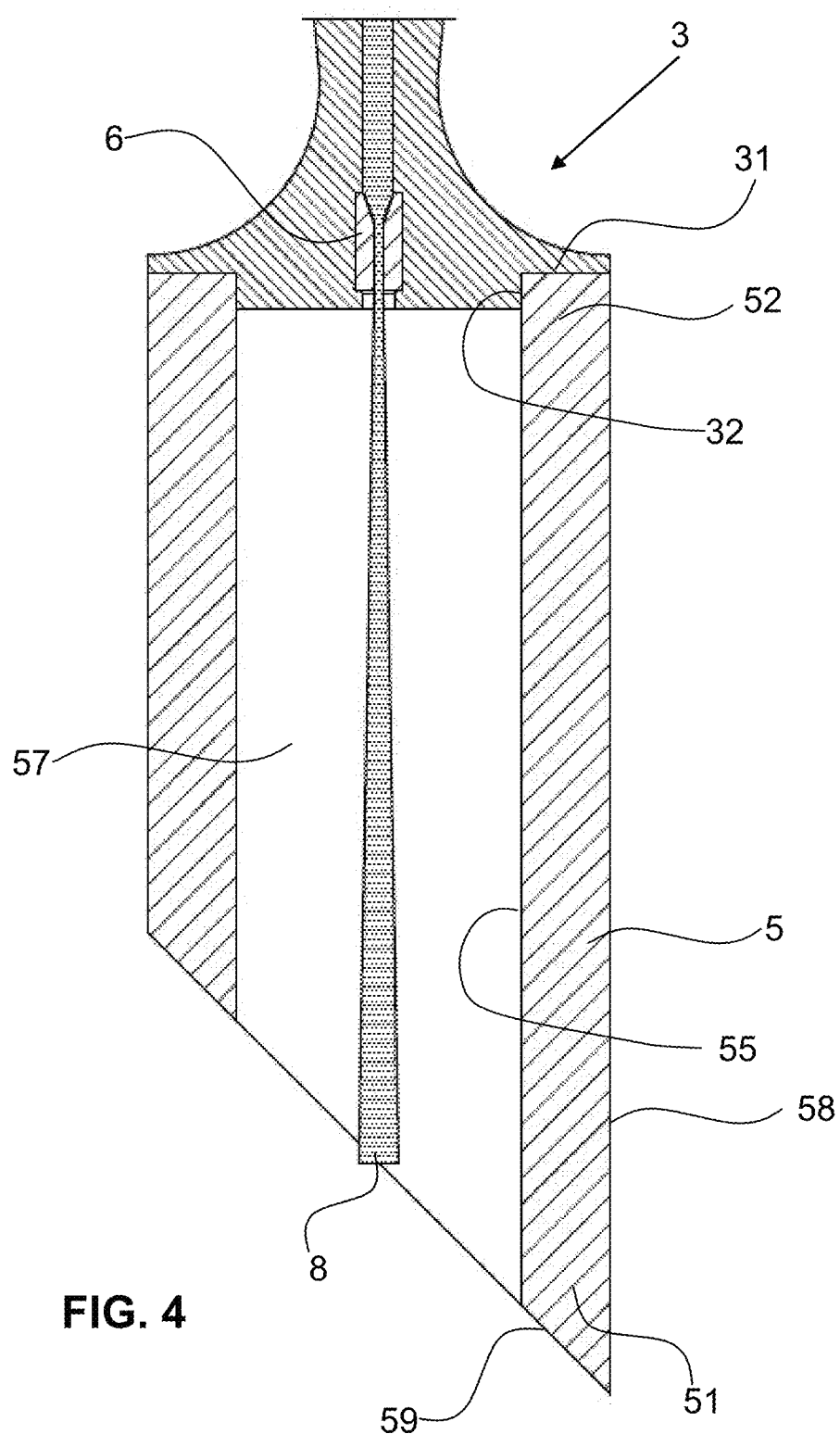
FIG. 4 shows a central sectional view of the front end of the handpiece with a porous body according to FIG. 3, with fluid jet.

FIG. 3 shows a perspective view of a second embodiment of the handpiece 1 according to the invention with a fluid jet 8, while FIG. 4 shows a central sectional view of the front end 3 thereof. The first and second embodiments are largely identical. In contrast to the first embodiment, the porous body 5 of the second embodiment has a beveled contact area 51 and preferably has sharp-edged transitions between the contact surface 59 and the inner surface 55 and outer surface 58. The bevel is shown by the fact that the contact surface 59 extends at an angle other than 90° with respect to the jet direction. The angle depicted corresponds to approximately 45°.

Figure 5:
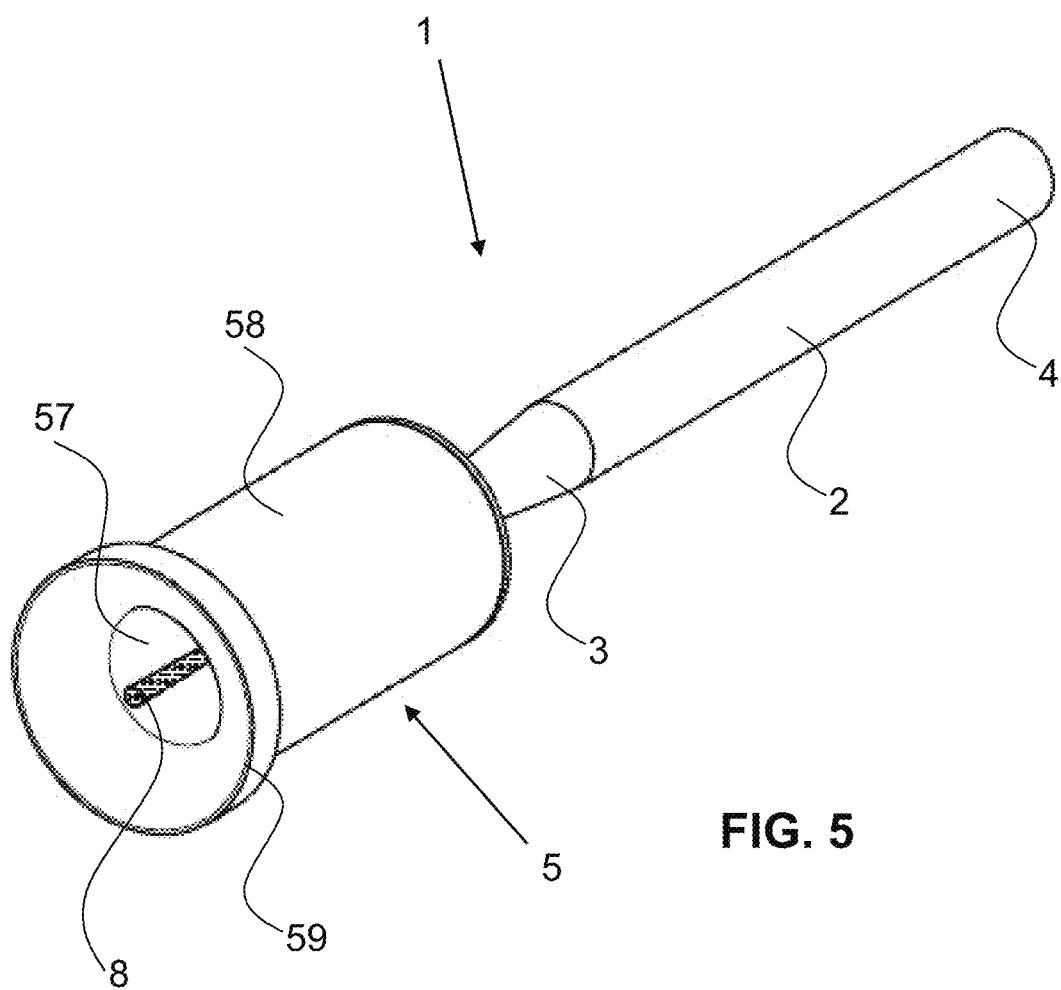
FIG. 5 shows a perspective view of a third embodiment of a handpiece according to the invention, with fluid jet.
Figure 6:
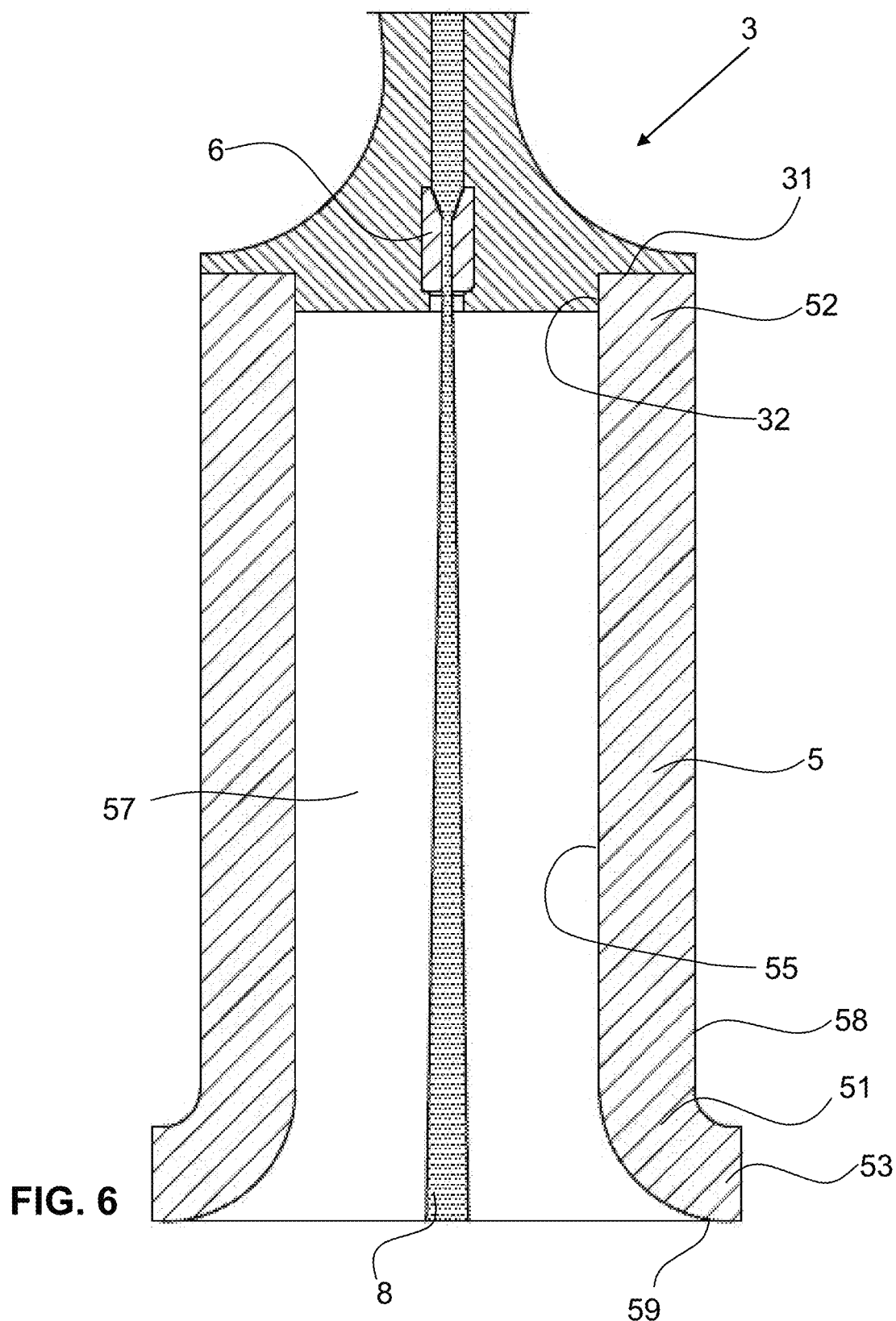
FIG. 6 shows a central sectional view of the front end of the handpiece with a porous body according to FIG. 5, with fluid jet.

FIG. 5 shows a perspective view of a third embodiment of a handpiece 1 according to the invention with a fluid jet 8, while FIG. 6 shows a central sectional view of the front end 3 thereof. The first, second and third embodiments are largely identical. In contrast to the first two embodiments, the porous body 5 of the third embodiment has an outwardly directed front collar 53 in the contact area 51. The transition between the front collar 53 and the inner surface 55 and outer surface 58 is rounded. The wall thickness of the porous body 5 is constant along its cylindrical length and does not change in the area of the front collar 53. The rounding of the transition from the contact surface 59 to the inner surface 55 creates a funnel-shaped area in the first through-opening 57 in the contact area 51.

Figure 7:
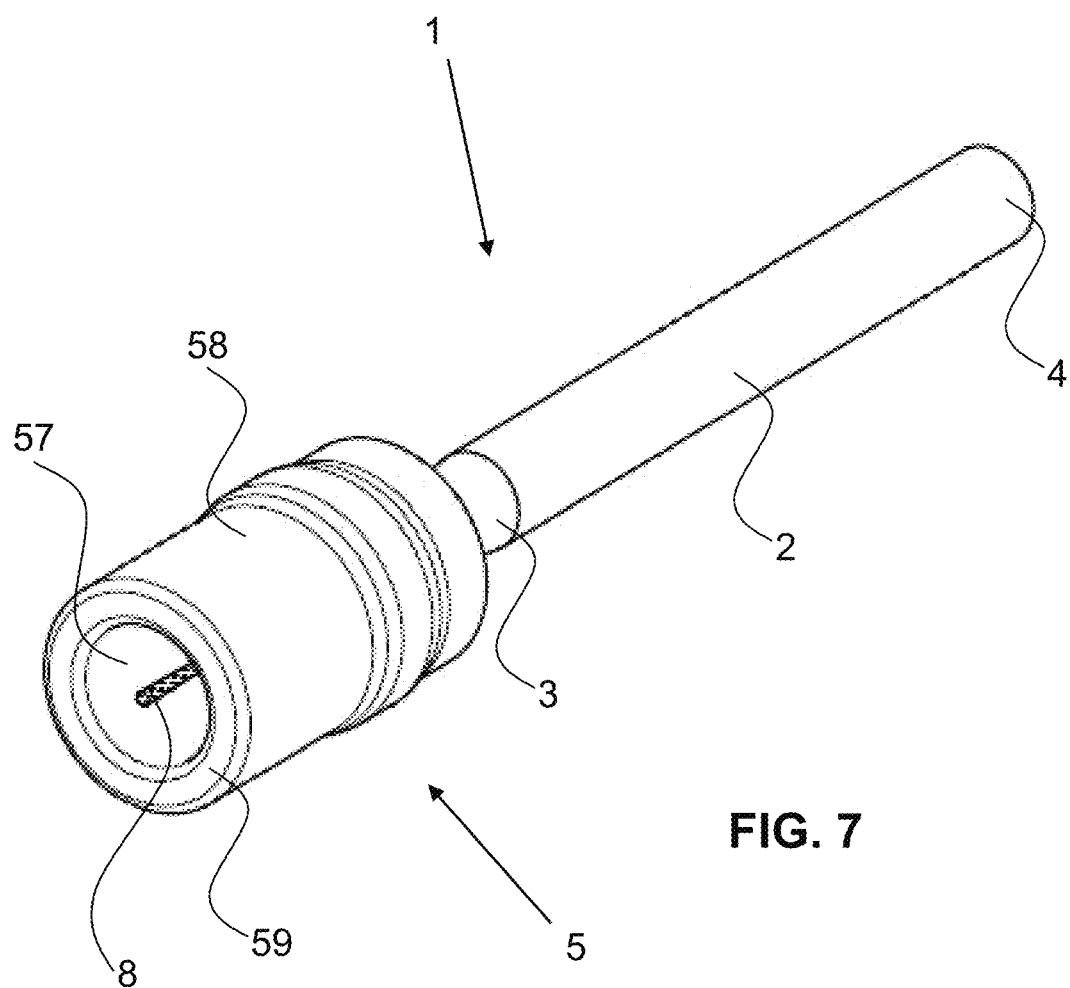
FIG. 7 shows a perspective view of a fourth embodiment of a handpiece according to the invention, with fluid jet.
Figure 8:
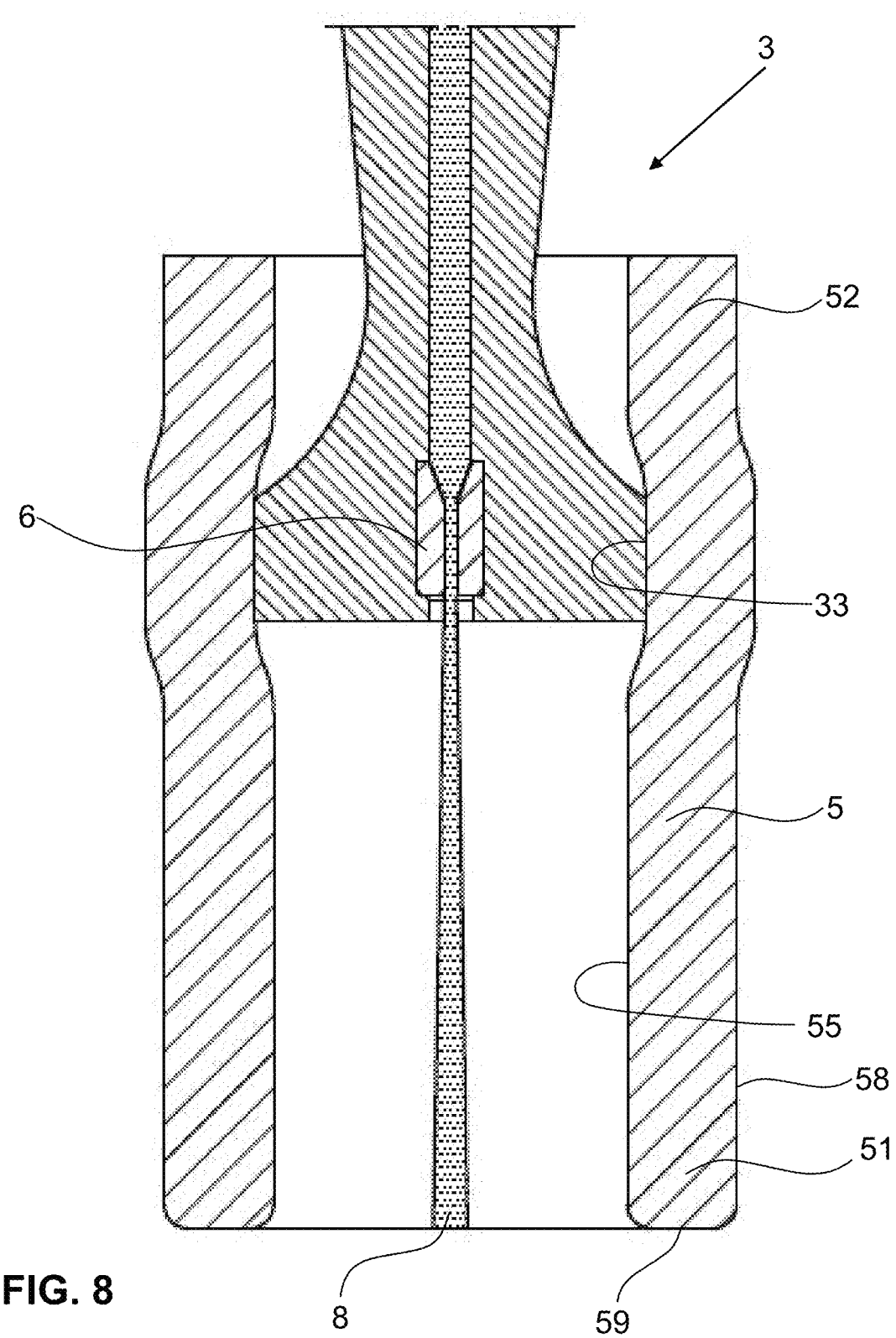
FIG. 8 shows a central sectional view of the front end of the handpiece with a porous body according to FIG. 7, with fluid jet.

FIG. 7 shows a perspective view of a fourth embodiment of a handpiece 1 according to the invention with a fluid jet 8, while FIG. 8 shows a central sectional view of the front end 3 thereof. The porous body 5 has largely the same design as that of the first embodiment. However, the front end 3 of the fourth embodiment is different than that of the first embodiment. However, the front end 3 is preferably likewise transparent. The first radial outer surface 33 of the front end 3 is dimensioned such that it can be inserted into the first through-opening 57. The diameter of the first radial outer surface 33 is preferably slightly larger than the internal diameter of the first through-opening 57. The inner surface 55 is movable and arranged clamped on the first radial outer surface 33 of the front end 3. The distance between the emergence opening 35 and the contact surface 59 is adjustable by a relative movement between the front end 3 and the porous body 5.

Figure 9:
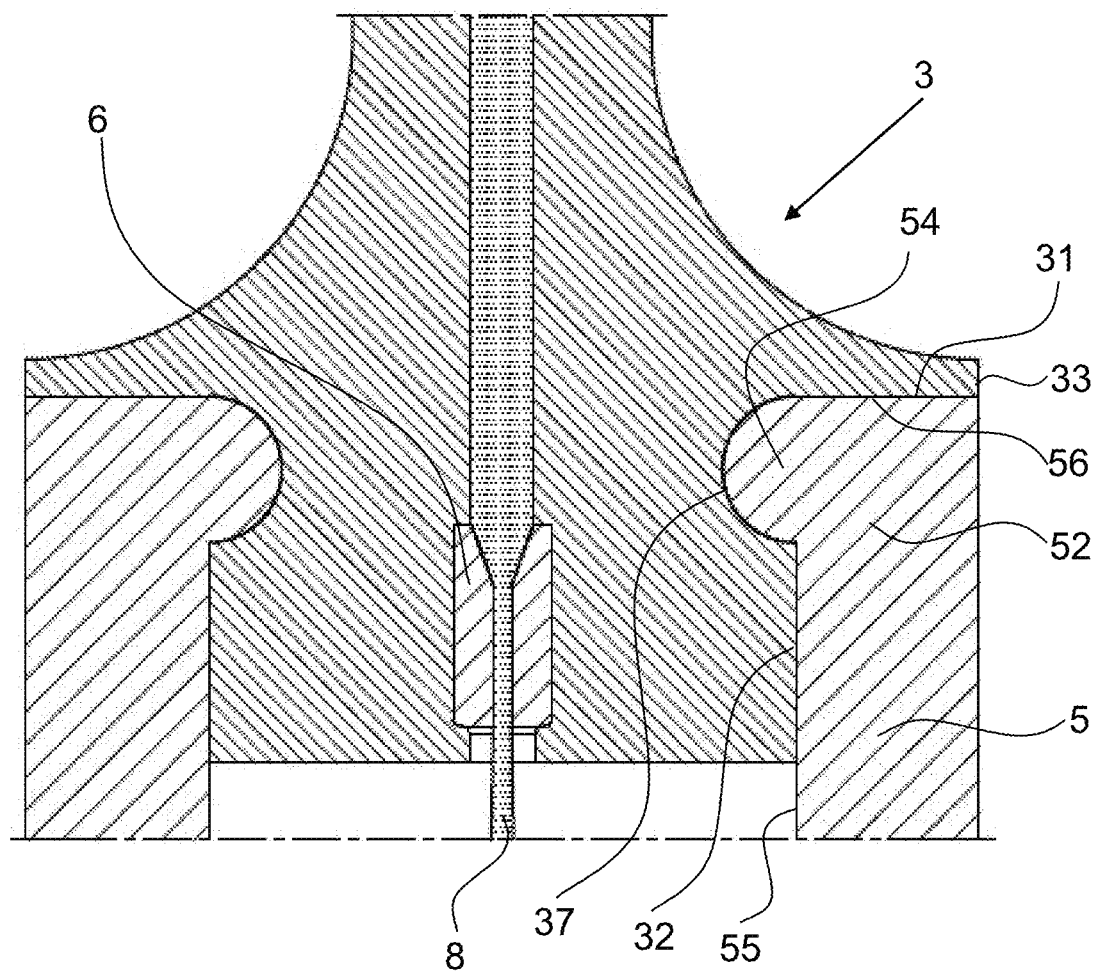
FIG. 9 shows a central sectional view of the front end of a handpiece with a porous body according to a further embodiment.

FIG. 9 shows a central sectional view of the front end of a handpiece with porous body according to a further embodiment. FIG. 9 basically shows an alternative releasable connection between the front end 3 and the porous body 5, as would be able to be used in the handpiece 1 of a first, a second or a third embodiment. Advantageously, the front end 3 of this embodiment is likewise transparent. In the rear area 52, the porous body 5 has an inwardly directed, circumferential rear collar 54, which engages in a corresponding recess in the front end 3 and forms a releasable connection 37 with the latter. A collar 54 is shown that has a cross section in the shape of a semicircle. The inner surface 55 of the porous body 5 is in releasable contact with the first radial limit 32 of the front end 3, and the rear face 56 of the porous body 5 is in releasable contact with the first axial limit 31 of the front end 3. By pulling on the porous body 5 in the jet direction, said porous body 5 can be removed from the front end.

Figure 10:
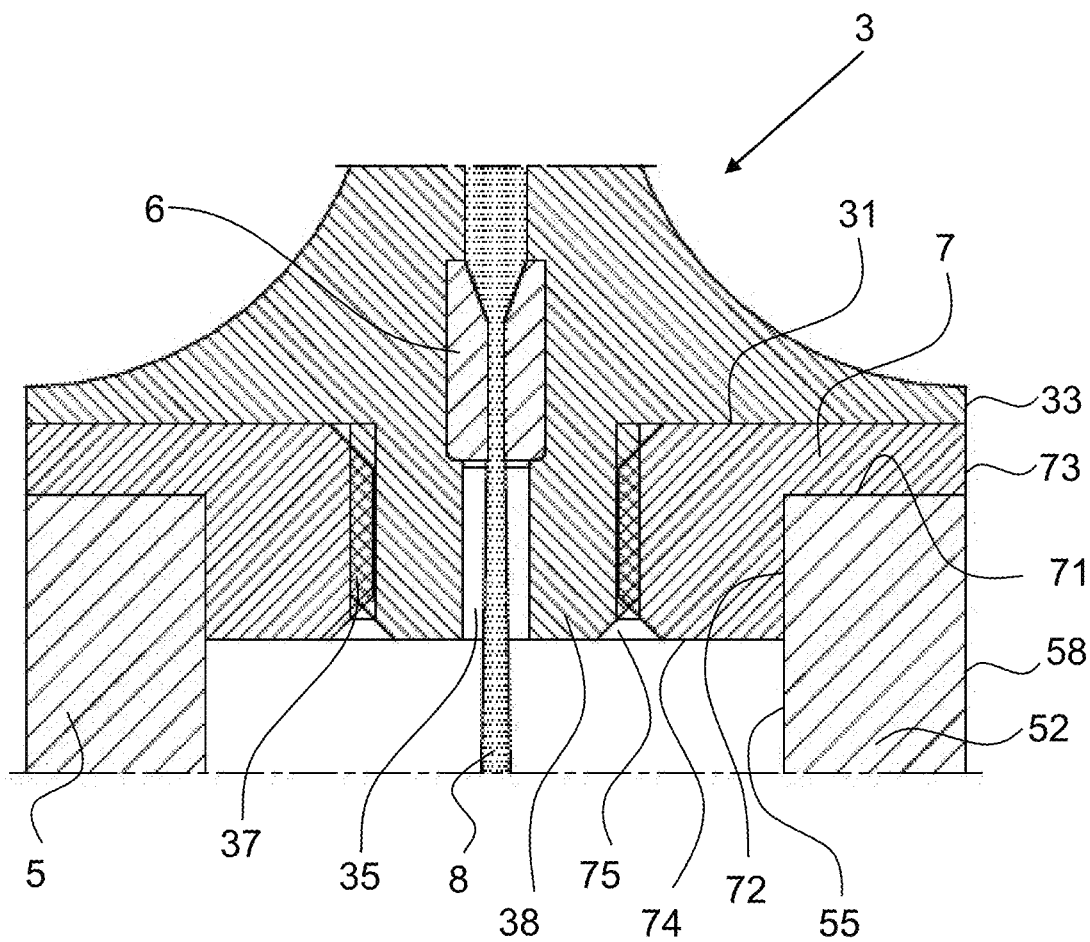
FIG. 10 shows a central sectional view of the front end of a handpiece with a porous body according to a further embodiment.

FIG. 10 shows a further alternative to the releasable connection of the front end 3 to the porous body 5. The porous body 5 is connectable releasably to the front end 3 by means of an adapter 7. The adapter 7 and the front end 3 are preferably transparent. The front end 3 has a connecting pin 38, which is arranged centrally and surrounds the emergence opening 35. The adapter has a central second through-opening 75, which is oriented coaxially with the porous body 5. The connecting pin 38 and the second through-opening 75 together form a releasable connection 37, here shown in the form of a screw connection. A second front face 74 of the adapter 7 has a cutout with a second axial limit surface 71 and a second radial limit surface 72 for receiving the porous body 5. The porous body 5 bears via the inner surface 55 on the second radial limit 72 of the adapter 7 and bears via the rear face 56 on the second axial limit 71 of the adapter 7. The outer surface 58 of the porous body 5 is flush with a second radial outer surface 73 of the adapter 7.

Figure 11:
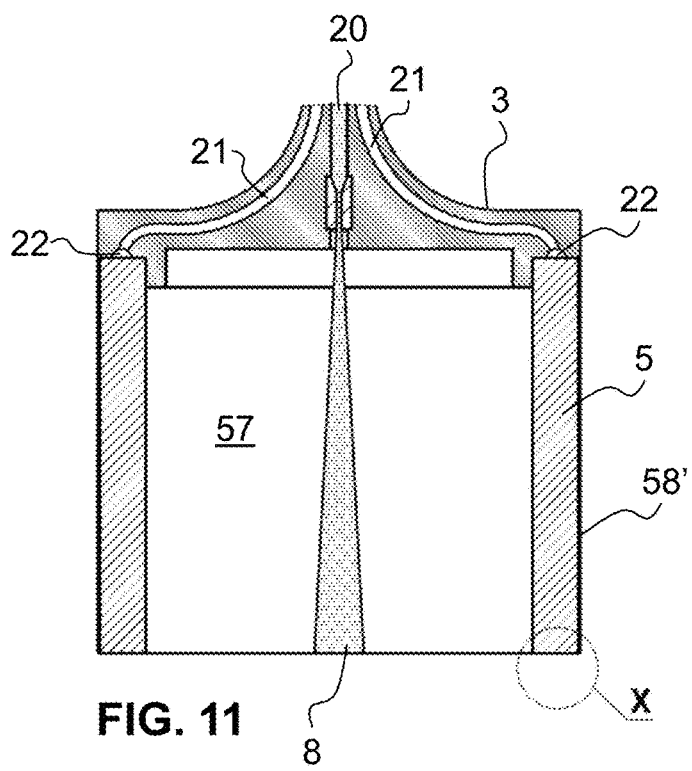
FIG. 11 shows a central sectional view of a further embodiment according to the invention with suction.
Figure 12:
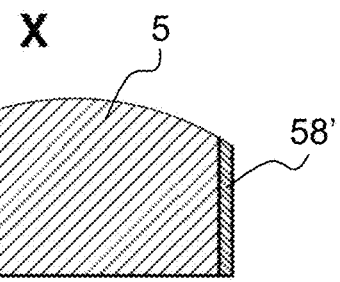
FIG. 12 shows an enlarged view of a detail X according to FIG. 11.

An embodiment with a tight outer skin 58' and with a suction system is provided in FIG. 11. The tight outer skin 58' can be seen clearly in FIG. 12. It is preferably a layer which is applied to the porous body and which completely surrounds the outer circumference of the porous body 5 and provides an airtight and liquid-tight seal from the outside. It preferably covers the jacket area but leaves the lower face 59 of the porous body 5 free, the lower face therefore being configured in an open-pored manner. In alternative embodiments, this lower face is also covered.

The main body 2 has at least one suction channel dividing up in the front end 3 of the handpiece 1 into suction channels 21 and leading to the upper face of the porous body. Several suction channels 21 may already be present in the main body 2 and, for example, do not divide up any further. An annular distributor channel 22 is preferably present on said face, said distributor channel 22 being open toward the porous body 5, or open in sections, and ensuring that the underpressure applied via the suction channel is distributed uniformly across the front circumference of the porous body 5. In this embodiment, the suction takes place via the pores of the porous body 5.

Figure 13:
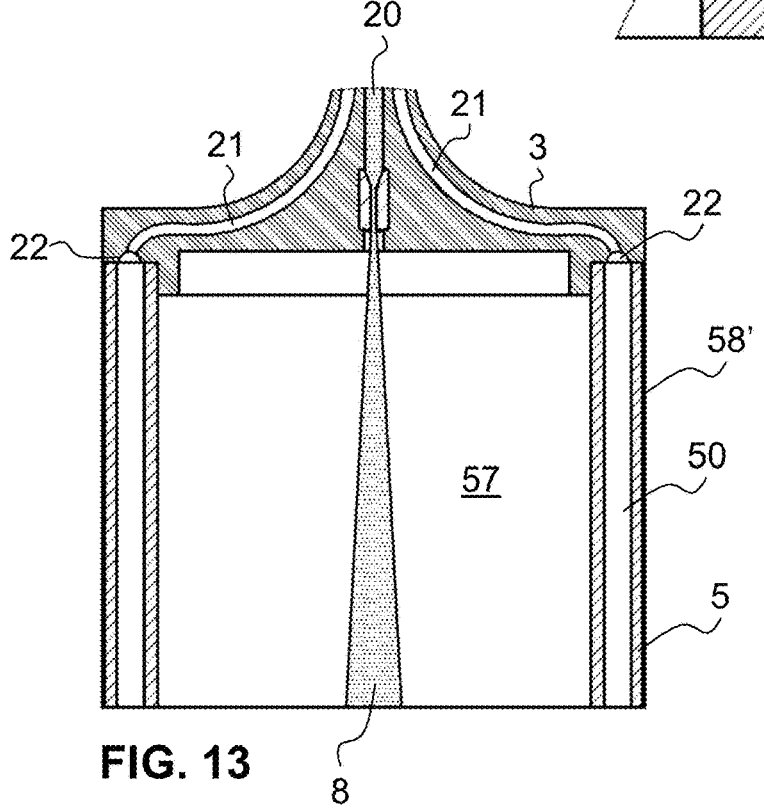
FIG. 13 shows a central sectional view of a further embodiment according to the invention with suction.

In the embodiment according to FIG. 13, the porous body 5 has several suction channels 50 preferably distributed uniformly about its circumference. These suction channels 50 extend parallel to the jacket surface and/or parallel to the jet direction of the fluid jet 8. The suction channels 50 preferably extend rectilinearly and have a larger diameter than the average pore size of the porous body 5. Their diameter is preferably many times the average pore size. These vertical suction channels 50 preferably extend as far as the lower face 59 of the porous body and are therefore open at the bottom. However, they can also terminate farther up or can be closed by the tight outer skin.

Depending on the embodiment, the distributor channel 22 is open exclusively toward these suction channels 50 or it also opens toward other locations of the face of the porous body. This embodiment with the suction channels 50 has the advantage that the suction still functions even when the porous body 5 is strongly saturated, since blocking of the pores is prevented.

Figure 14:
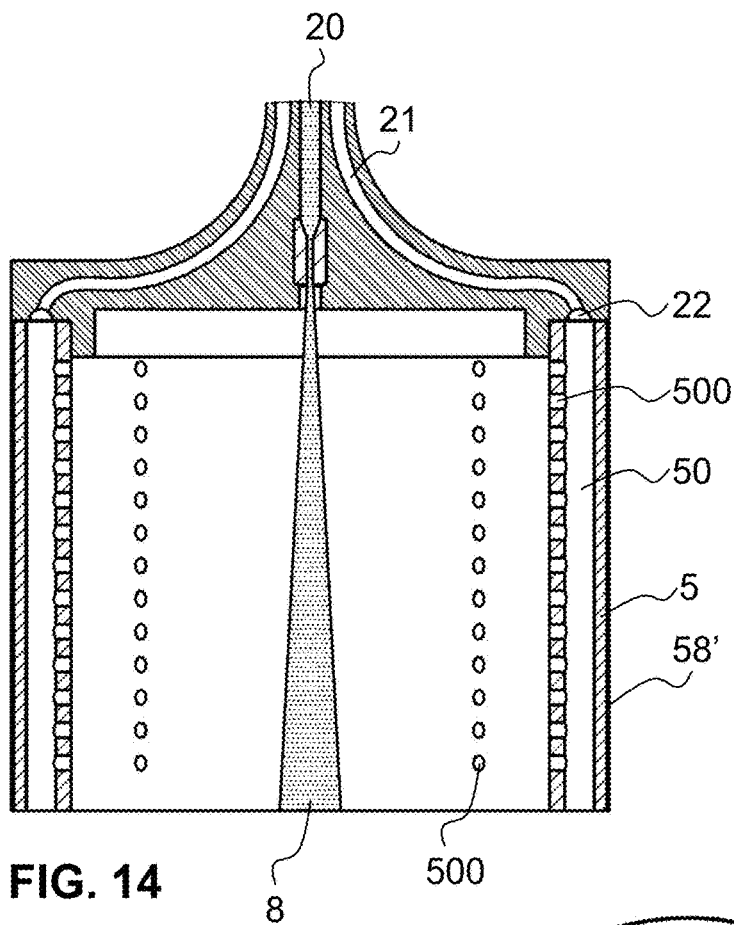
FIG. 14 shows a central sectional view of a further embodiment according to the invention with suction.
Figure 15:
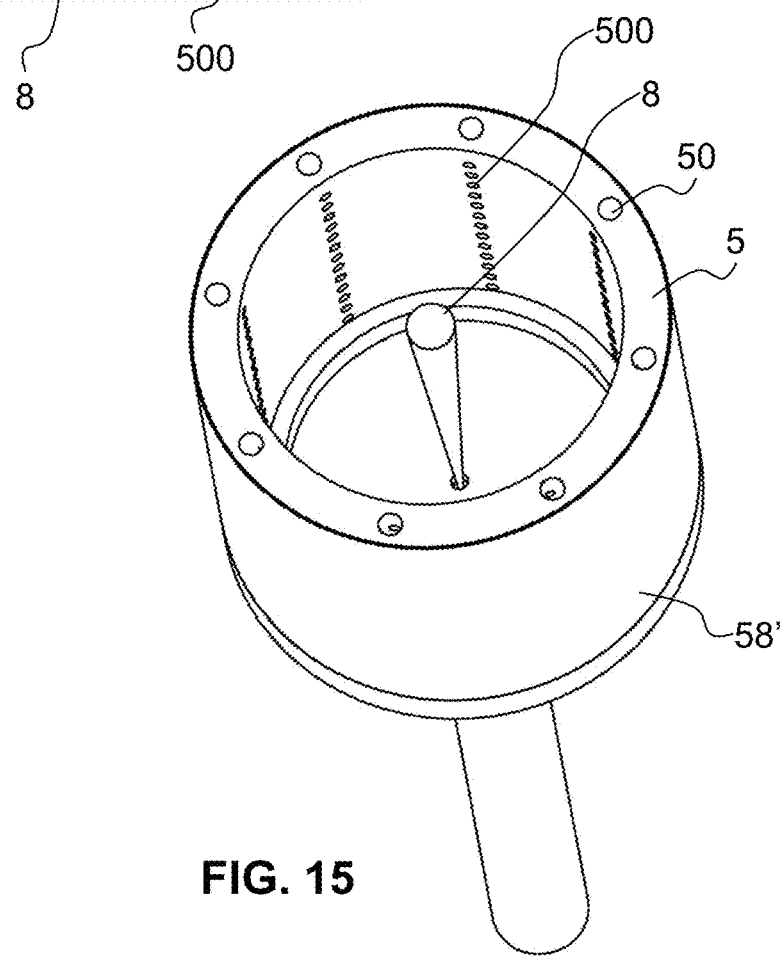
FIG. 15 shows a perspective view of the embodiment according to FIG. 14 from below.
Figure 19:
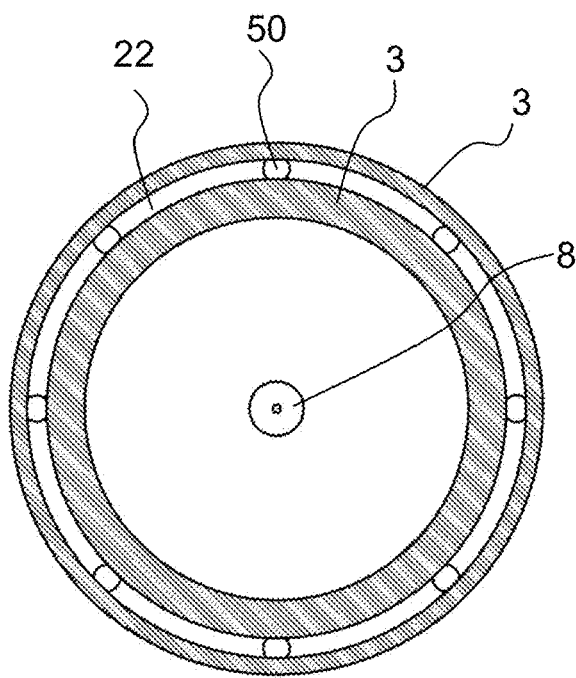
FIG. 19 shows a section through the embodiment according to FIG. 18 along A-A.
Figure 18:
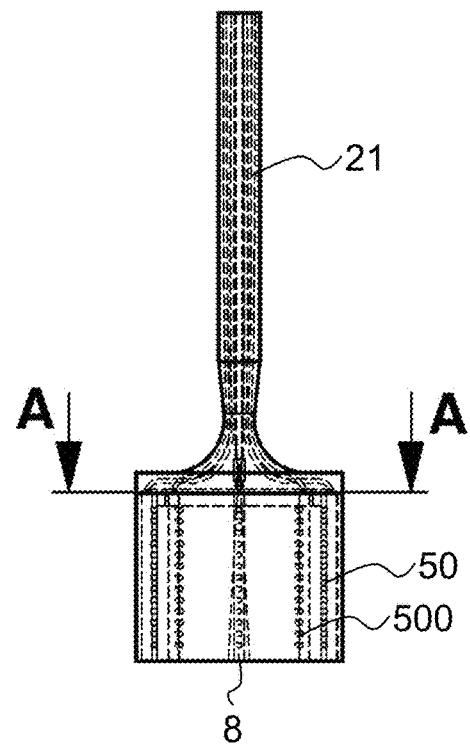
FIG. 18 shows a central sectional view of the embodiment according to FIG. 14.

In the embodiment according to FIGS. 14 and 15, radially extending suction channels 500 are present in addition to the axially extending suction channels 50. These radially extending suction channels 500 connect the axial suction channels 50 to the hollow interior 57 of the porous body 5, i.e. the space through which the fluid jet passes unimpeded. The radial suction channels 500 are preferably distributed along the entire length of the axial suction channels 50. The annular distributor channel 22 leading to the axial suction channels 50 can be seen clearly in FIGS. 18 and 19.

Figure 16:
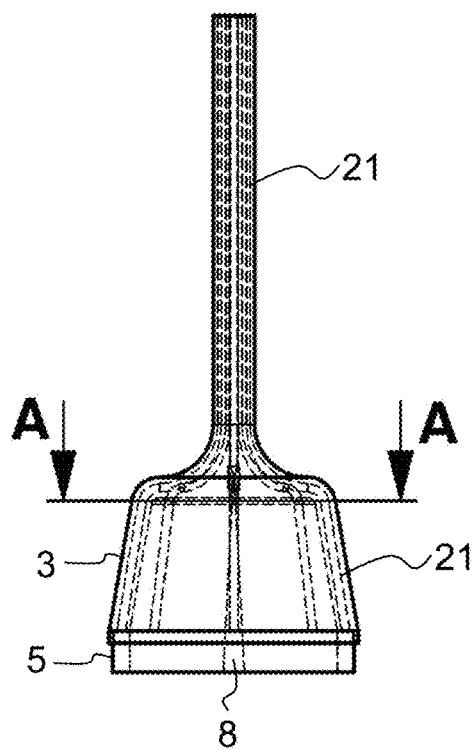
FIG. 16 shows a central sectional view of a further embodiment according to the invention with suction.
Figure 17:
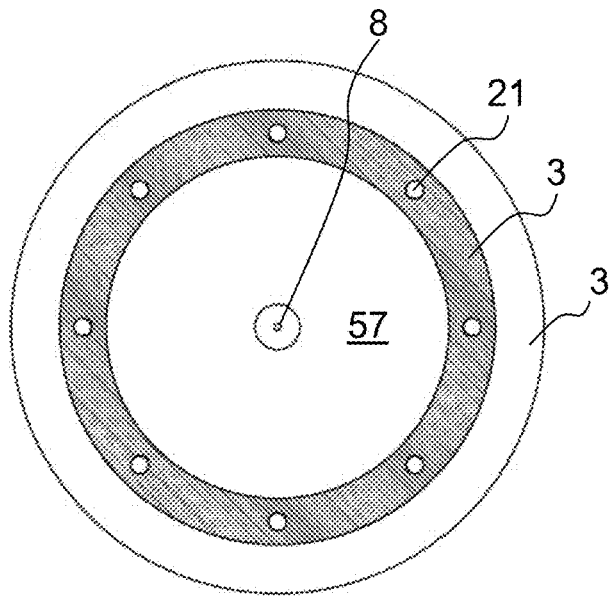
FIG. 17 shows a section through the embodiment according to FIG. 16 along A-A.

FIGS. 16 and 17 show a further embodiment. The suction channels 21 leading from the direction of the main body 2 extend through the front end 3 and open directly into the porous body 5. The front end 3 is relatively large and preferably has a conical shape widening toward the free end. The porous body 5 secured thereon has a cylindrical shape here and is relatively short in the jet direction.

Figure 20:
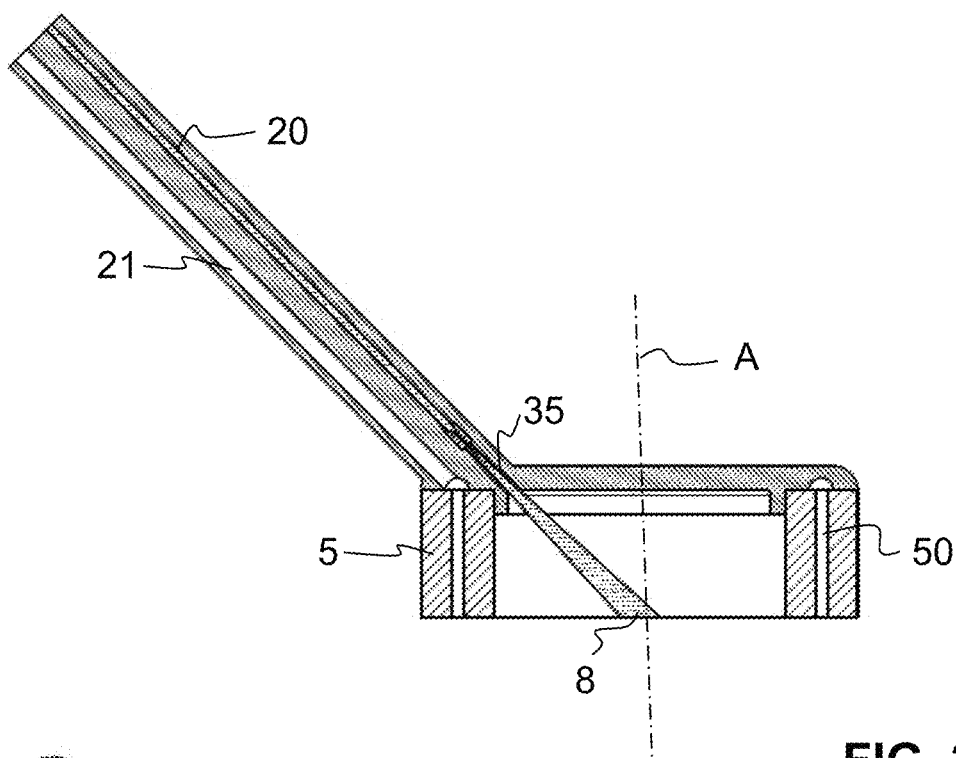
FIG. 20 shows a central sectional view of a further embodiment according to the invention.
Figure 21:
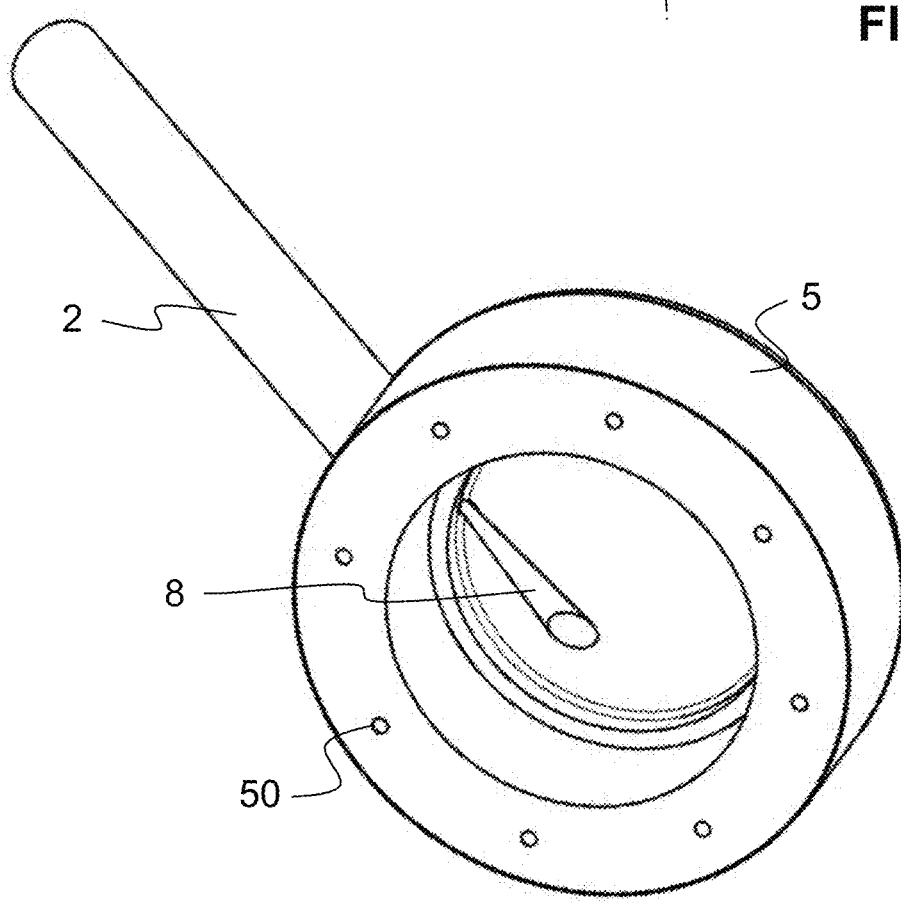
FIG. 21 shows a perspective view of the embodiment according to FIG. 20 from below.

In the embodiment according to FIGS. 20 and 21, the emergence opening 35 and the fluid channel 20 are oriented obliquely with respect to the longitudinal central axis A, such that the emerging fluid jet extends at an angle to the longitudinal central axis A. The angle is preferably approximately 45°. The hollow interior of the porous body 5 is preferably so dimensioned that the fluid jet does not strike an inner wall of the body. A suction system may be present. In other embodiments, no suction system is present. Moreover, the porous body can, as shown, have one or more axial and/or radial suction channels. In other embodiments, it has no suction channels. Otherwise, the features described for the other embodiments can also be used in an angled arrangement of the fluid jet. In particular, the porous bodies described above with their shapes and suction channels can also be used in this embodiment. In this example, only a single suction channel 21 is present in the handpiece 2 and opens into the annular distributor channel 22. However, it is also possible here for several suction channels 21 to be arranged in the handpiece 2.

Figure 22:
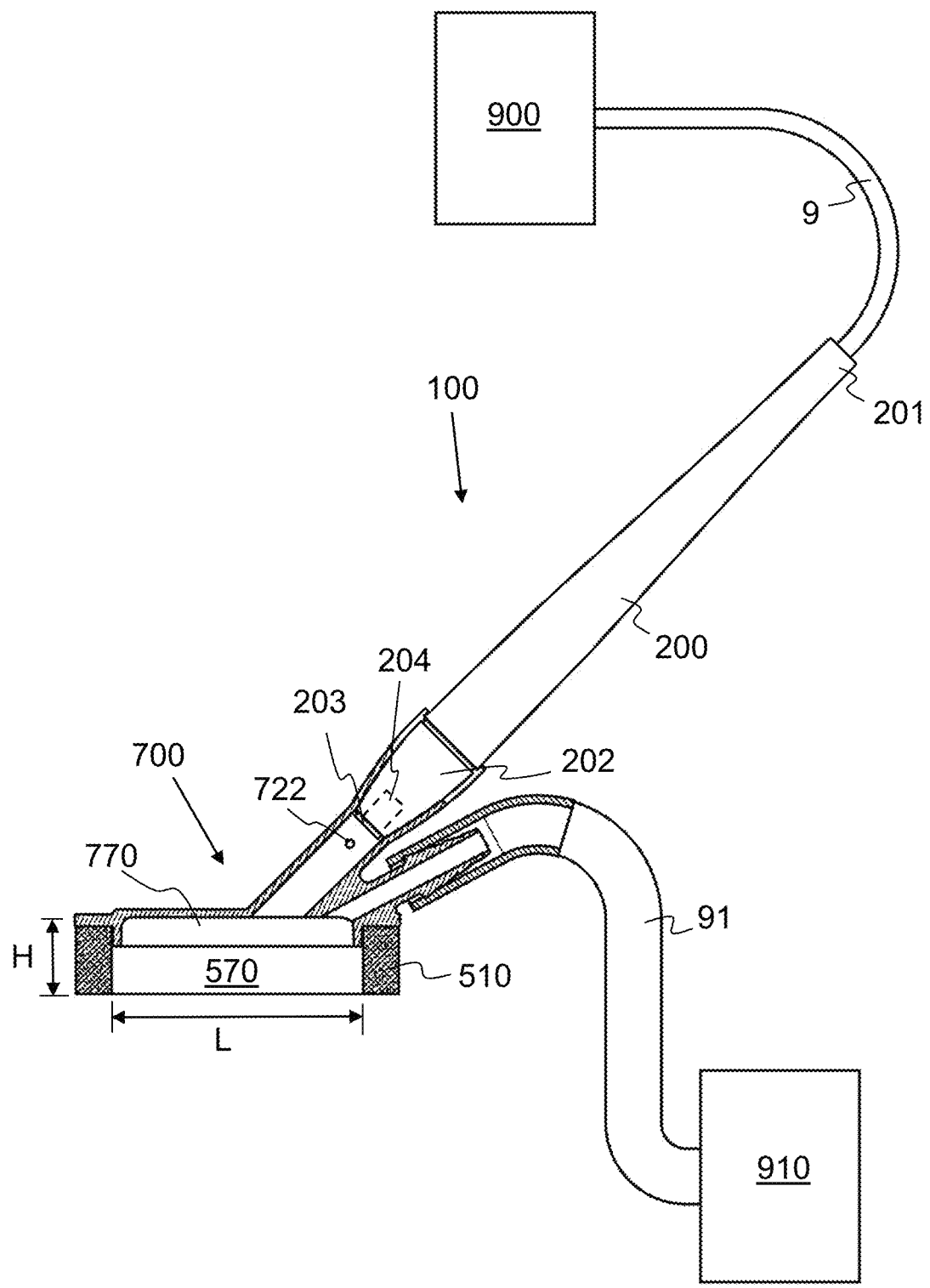
FIG. 22 shows schematically an inventive system for cleansing with a handpiece comprising an adapter according to a further embodiment, wherein the adapter is shown in cross-section.

FIGS. 22 to 25 show a further preferred embodiment of the invention claimed. FIG. 22 shows a system for cleansing wounds with a fluid jet, for example by removing biological tissue. The system comprises a pressure pump 900 for providing a fluid jet, such as a water jet. A fluid line 90 connecting the pump 900 with a handpiece 100. The handpiece 100 comprising handpiece body 200, an adapter 700 and a porous body 510. The handpiece body 200 has a first end 201 to which the fluid line 90 is attached and a second end 203 having an emergence opening for emerging the fluid jet. The emergence opening is preferably formed by a nozzle 204 reducing the size of the fluid jet such that it is optimized for cleansing the wound, i.e. for the debridement. The nozzle preferably comprises a plate with at leas one hole defining a central channel wick defines the shape and size of the fluid jet emerging the nozzle. Preferably the plate is welded to the lower end of the handpiece body 200, especially of a lower end piece part 202 of the handpiece body 200.

Preferred values for the fluid pressure emerging the handpiece body 200 are 100 bar to 160 bar. Preferred values for the diameter of the emergence opening are 0.05 mm to 0.2 mm. Preferred values for the area of the emergence opening are . . . 0.002 mm$^2$ to 0.031 mm$^2$. Preferred shapes of the fluid emerging the handpiece body 200 are a small circle or a line.

For example, a pressure pump can be used in this system as described in U.S. Pat. No. 10,550,839 B2 or U.S. Pat. No. 10,653,439 B2. For example, the handpiece can be shaped as described in US 2016/0346794 A1 or US 2018/0126392.

The adapter 700 is releasably attached to the second end 203 of the handpiece body 200. In preferred embodiments, the adapter 700 is further releasably attached to a suction pump 910, wherein a suction line 91 preferably extends between the adapter 700 and the suction pump 910.

Figure 23:
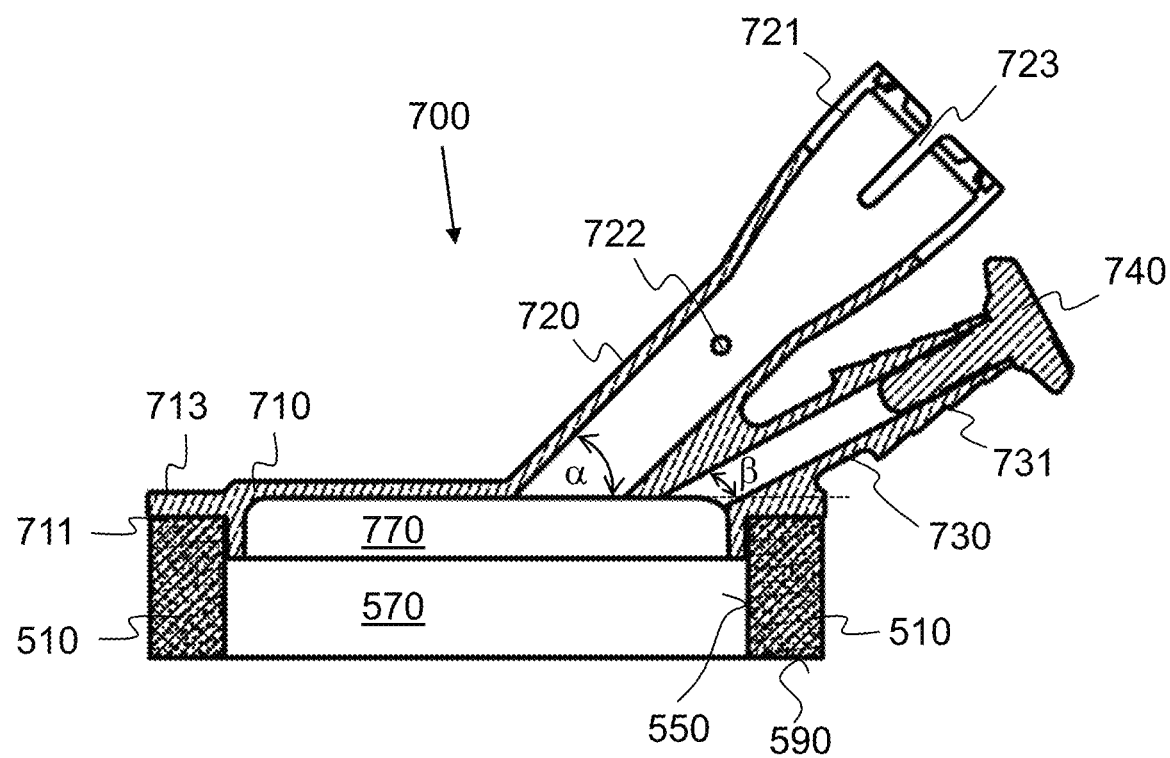
FIG. 23 shows a cross-sectional view of the adapter according to FIG. 22.
Figure 24:
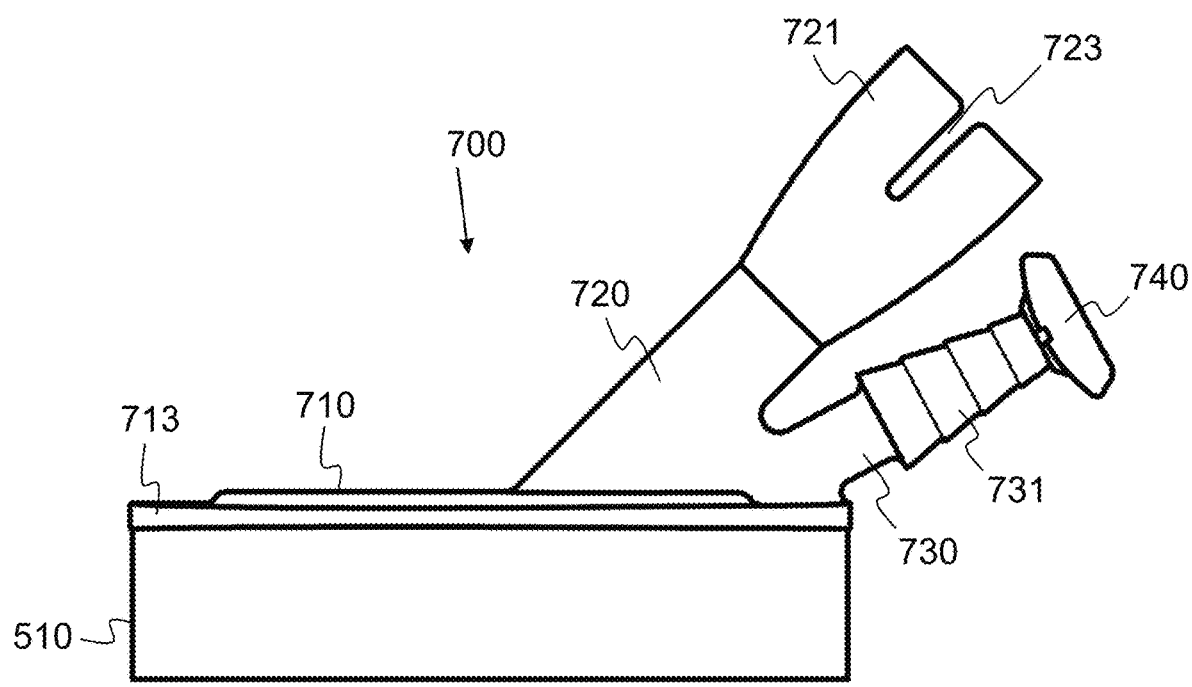
FIG. 24 shows a side view of the adapter according to FIG. 22.
Figure 25:
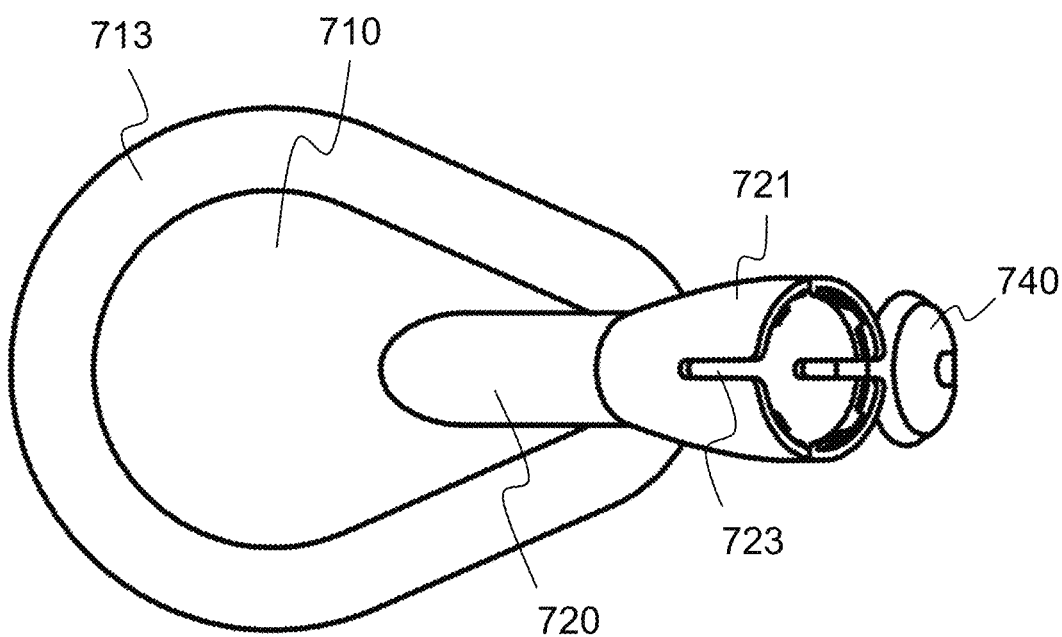
FIG. 25 shows a top view of the adapter according to FIG. 22.

FIGS. 23 to 25 show the adapter 700 and the porous body 510 attached to the adapter 700. The adapter 700 and the porous body 510 form a unit, preferably a disposable unit.

The adapter 700 comprises a basic body 710. The basic body 710 has a top view and/or a bottom view which is/are preferably in the shape of a teardrop. The teardrop shape has a rounded periphery with a smaller end having a smaller radius and a larger end having a larger radius.

The basic body 710 has preferably a flat upper surface. The basic body 710 comprises an outer circumferential rim 710, extending parallel to an upper surface of the basic body 710 and an inner circumferential rib 712 extending in a perpendicular direction to the upper surface of the basic body 710. A lower surface 711 of rim 713 and an outer surface of the rib 712 form attachment areas to which the porous body 510 is fixed. Preferably, the porous body 510 is glued or welded to these areas.

The porous body 510 has preferably the shape of a cylinder with a cross-section, which corresponds to the rim 713 of the basic body 710. I.e. in this example, the cross-section of the porous body 510 has a teardrop shape. The porous body 510 forms a circumferentially closed element, which is open on the top and at the bottom and which encloses a free inner space 570.

The free end of the porous body 510, which extends at the opposite side of the basic body 710 preferably defines a lower surface 590, which is preferably flat or otherwise shaped to be placed on the patient's skin around the patient's wound. An inner surface 550 surrounding the free inner space 570 is preferably flat and porous.

The porous body is preferably not coated. Preferably it is an open-pored sponge.

Preferably, the porous body 510 is made of polyurethane. Preferably, the porous body 510 is made of a soft material.

The basic body 710 defines an inner space 770, which is surrounded by the inner rib 713 and which leads to an inner space 570 defined by the porous body 510. The two inner spaces 770 and 570 therefore form a common inner space of the unit formed by the adapter and the porous body. The inner space 570 of the porous body 510 leads outside. In use, the lower surface 590 forms a contact area and lays on a patient's skin surrounding a patient's wound and the inner space 570 of porous body 510 is arranged above this wound.

A connection part 720 extends from the basic body 710, preferably at an angle α with regard to the upper surface of the basic body 710. The angle α is other than 0° and 90° and it is preferably about 45°.

The connection part 720 ends in a receiving part 721, which receives the fluid line 90. The receiving part 721 preferably comprises at least one slit 723, which renders the receiving part 721 to be slightly resilient and which ensures that the fluid line 90 is hold in a fluid tight way but which also ensures that the connection between receiving part 721 and fluid line 90 can easily been released. In the embodiment shown, four slits 723 are present. However, there can be also more or less slits 723.

In preferred embodiments, a second connection part 730 extends from the asic body 710. Preferably, it the second connection part 730 is located adjacent to the first connection part 720. The second connection part 730 extends in an angle β with regard to a surface of the basic body 710. The angle β is preferably smaller than the angle α, preferably the angle β is about 20°.

The second connection part 730 comprises an end 731 which is shaped to be tightly but releasably received within the suction line 91. Preferably the end 731 comprises outer ribs enabling a fir tree connection as shown in FIGS. 23 and 24.

The first connection part 720 preferably comprises at least one through opening 722 connection the interior of the first connection part and the inner space 770 to the outside. This avoids a to high underpressure within the inner spaces 770 and 570 during suction.

In case no suction pump 910 is used, the end 731 of the second connection part 730 is closed with a plug 740.

The size and shape of the basic body 710 and the porous body 510 as well as the arrangement of the first connection part 720 is preferably such that the fluid jet enters the inner space 770 of the basic body at an angle but at a central line of the inner space 700 and that the fluid jet, when extending through the inner space 700 and the inner space 570 of both the basic body 710 and the porous body 550 does not reach the inner surfaces. This means that the height H of the combination of basic body 710 and porous body 550 and the length L of the inner spaces 770, 570 are chosen with regard to the angle α. Having an angle α of about 45°, the length L is preferably about 47 mm and the height H is preferably about 15 mm. The teardrop shape has a smaller extension and a longer extension, wherein the length L is preferably extending along the direction of the longer extension.

At least a window within the upper part of the main body 710 of the adapter 700, preferably the whole upper surface of the main body and most preferably the whole adapter 700 is made of a transparent material. Preferably, it is made of polycarbonate. This enables a perfect view onto the wound during treatment of the wound, especially when the upper surface of the basic body is a plane surface. The progress of the treatment can therefore be watched without having to remove the adapter and the porous body from the patient's skin.

The fluid jet is used to clean the wound and to remove organic tissues, i.e. for the debridement of the wound. The suction line is used to remove the fluid and the removed particles, especially the organic tissues, from the inner space 770, 570.

Since the unit consisting of the adapter 700 and the porous body 510 can be removed quite easily from the handpiece body 200, this unit can be made as a one-use disposable article.

The arrangement of the first connection part 720 at an angle to the upper surface of the basic body 710 and preferably also to the lower surface 590 of the porous body enables an easy assembly of the device. The adapter with the porous body can sealed in a sterile package. This package can be opened on the top, giving the first connection part 720 free. The handpiece body 200 can be moved with its second end 203 into the first connection part 720 and the whole adapter 700 can be lifted together with the porous body 550 out of the packaging without having to touch these elements at all. It can be placed immediately on the patient's skin, thereby ensuring sterile treatment.

The handpiece according to the invention combines the advantages of cleansing by a fluid jet with the advantages of mechanical cleansing and, at the same time, provides effective protection against aerosols.

The invention claimed is:

1. A system for cleansing wounds with a fluid jet, the system comprising,
   a handpiece body with a nozzle for emerging the fluid jet,
   a fluid line connected with the handpiece body,
   an adapter holding a porous body, the adapter being releasably connected to the handpiece body,
   wherein the porous body comprises a lower surface which is shaped to be placed on a patient's skin around a wound to be cleaned,
   wherein the adapter and the porous body comprise a free inner space into which the fluid jet emerges when leaving the nozzle, and
   wherein the adapter is at least partially transparent, thereby enabling a view into the inner space of the adapter and the porous body and thereby enabling a view of the wound that is to be cleaned.

2. The system according to claim 1 wherein the fluid jet passes the free inner space unimpeded before reaching the patient's wound.

3. The system according to claim 1 wherein the adapter and the porous body have a cross section in an elongated shape.

4. The system according to claim 1 wherein the adapter and the porous body have a cross section in the shape of a teardrop, the teardrop having a rounded periphery with a smaller end having a smaller radius and a larger end having a larger radius.

5. The system according to claim 4 wherein the adapter comprises a first connection part for connecting the adapter with the handpiece body and wherein the first connection part is arranged at the smaller end of the teardrop-shaped adapter.

6. The system according to claim 5 wherein the adapter comprises a second connection part for connecting the adapter with a suction line and wherein the second connection part is arranged at the smaller end of the teardrop-shaped adapter.

7. The system according to claim 1 wherein at least the upper surface of the adapter is transparent.

8. The system according to claim 1 wherein the whole adapter is transparent.

9. The system according to claim 1 wherein the porous body is fixed to the adapter.

10. The system according to claim 1 wherein the porous body is glued or welded to the adapter.

11. The system according to claim 1 wherein the porous body is made of a sponge, fleece or knit material.

12. The system according to claim 1 wherein the porous body has a through-opening which is penetrated by the fluid jet.

13. The system according to claim 1 wherein the adapter comprises a basic body and a first connection part for connecting the adapter with the handpiece body and wherein the first connection part is arranged at an angle with regard to an upper surface of the basic body, the angle being other than 0° and 90°.

14. The system according to claim 13 wherein the nozzle and the first connection part of the adapter allow the fluid jet to emerge in a direction which is at an angle with respect to a longitudinal central axis of the porous body.

15. The system according to claim 1 wherein the adapter comprises an outer rim with a horizontal lower surface and a vertical circumferential rib forming a vertical surface and wherein the porous body is fixed at least to one of the horizontal lower surface and the vertical circumferential rib.

16. The system according to claim 1 wherein the porous body forms a circumferentially closed element with a straight vertical outer surface.

17. A unit comprising an adapter and a porous body of a system for cleansing wounds with a fluid jet, the system comprising
- a handpiece body with a nozzle for emerging the fluid jet,
- a fluid line connected with the handpiece body,
- the adapter holding the porous body, the adapter being releasably connected to the handpiece body,
- wherein the porous body comprises a lower surface which is shaped to be placed on a patient's skin around a wound to be cleaned,
- wherein the adapter and the porous body comprise a free inner space into which the fluid jet emerges when leaving the nozzle, and
- wherein the adapter is at least partially transparent, thereby enabling a view into the inner space of the adapter and the porous body and thereby enabling a view of the wound that is to be cleaned.

* * * * *